US012765881B2

(12) United States Patent
Kuo

(10) Patent No.: US 12,765,881 B2
(45) Date of Patent: Oct. 20, 2026

(54) PATIENT SPECIFIC INSTRUMENTATION FOR SURGICAL IMPLANTATION OF A FEMORAL COMPONENT

(71) Applicant: United States Government As Represented By The Department Of Veterans Affairs, Washington, DC (US)

(72) Inventor: Alfred Kuo, San Francisco, CA (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 18/787,264

(22) Filed: Jul. 29, 2024

(65) Prior Publication Data

US 2025/0032127 A1 Jan. 30, 2025

Related U.S. Application Data

(60) Provisional application No. 63/515,960, filed on Jul. 27, 2023.

(51) Int. Cl.
*A61B 17/15* (2006.01)
*A61B 17/74* (2006.01)

(52) U.S. Cl.
CPC ............ *A61B 17/155* (2013.01); *A61B 17/74* (2013.01)

(58) Field of Classification Search
CPC ..... A61B 17/15; A61B 17/154; A61B 17/155; A61B 17/157; A61B 17/158; A61B 17/74; A61B 17/742; A61B 17/744; A61B 17/746; A61B 17/748; A61B 17/1668
See application file for complete search history.

(56) References Cited

U.S. PATENT DOCUMENTS

| | | | | |
|---|---|---|---|---|
| 7,621,919 | B2 * | 11/2009 | Williams, III ......... | A61B 17/15 606/87 |
| 9,005,207 | B2 * | 4/2015 | Dodds ................ | A61B 17/1764 606/88 |
| 2009/0222016 | A1 * | 9/2009 | Park ...................... | A61F 2/3609 700/98 |
| 2019/0374237 | A1 * | 12/2019 | Metzger ............ | A61B 17/1764 |
| 2022/0313286 | A1 * | 10/2022 | Sánchez Álvarez ... | A61B 34/10 |

* cited by examiner

*Primary Examiner* — Si Ming Ku
(74) *Attorney, Agent, or Firm* — Ballard Spahr LLP

(57) ABSTRACT

An orthopedic surgical assembly are configured to be received on a neck of a femur between a head and a shaft of the femur. The embodiment may include a base portion with a body portion defining a contoured recess, wherein the contoured recess is configured to be received adjacent a portion of the neck of the femur. A first guide plate may include a mounting tab and a cutting slot, the mounting tab being configured to be selectively coupled to the base portion so that the cutting slot is disposed adjacent the neck of the femur in a first position.

16 Claims, 6 Drawing Sheets

PATIENT SPECIFIC INSTRUMENTATION FOR SURGICAL IMPLANTATION OF A FEMORAL COMPONENT

CROSS-REFERENCE TO RELATED APPLICATION

The application claims priority to and the benefit of the filing date of U.S. Provisional Patent Application No. 63/515,960, filed Jul. 27, 2023, the entirety of which is hereby incorporated by reference herein.

FIELD

The disclosure is generally related to medical devices and procedures and, more particularly, to an orthopedic surgical cutting guide and methods of use thereof that facilitate the removal of a head of a femur during a hip replacement surgery.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a head 12 of a patient's femur is partially or totally replaced by a prosthetic stem 20 and femoral head, as shown in FIGS. 7A and 7B.

To facilitate the replacement of the natural joint with a prosthesis, orthopedic surgeons use a variety of orthopedic surgical instruments such as, for example, cutting blocks, drill guides, milling guides, and other surgical instruments. Typically, the orthopedic surgical instruments are generic with respect to the patient such that the same orthopedic surgical instrument may be used on a number of different patients during similar orthopedic surgical procedures. Of course, different patients are differently sized, and therefore one size of an orthopedic surgical instrument that may be suited for one patient may not be ideal for use on a smaller patient. For example, a cutting block for use on the femur of a large person may lead to an unnecessarily large incision on a smaller patient and, therefore, additional tissue trauma, as the same size block must be positioned within the patient.

However, the orthopedic surgical instruments may also be customized to a specific patient. Such customized patient-specific orthopedic surgical instruments are surgical tools for use by a surgeon in performing an orthopedic surgical procedure that is intended, and configured, for use on a particular patient. It should be appreciated that these instruments are distinct from standard, non-patient specific orthopedic surgical instruments that are intended for use on a variety of different patients. These customized patient-specific orthopedic surgical instruments are distinct from orthopedic prostheses, whether patient-specific or generic, which are surgically implanted in the body of the patient. Rather, customized patient-specific orthopedic surgical instruments are used by an orthopedic surgeon to assist in the implantation of orthopedic prostheses. However, although patient-specific orthopedic surgical instruments may lead to reduced tissue trauma and surgical exposure, these known instruments are typically unitarily formed and do not allow for the cutting plane placement or angle to be adjusted once the patient-specific instrument is formed. As such, should a surgeon desire to change the position of the cutting plane, additional time is required to produce an entirely new patient-specific surgical assembly.

From the foregoing, one recognizes the need for improved patient-specific orthopedic surgical instruments that allow flexibility for the surgeon and decreased time of production.

SUMMARY

Embodiments of the disclosed orthopedic surgical assembly are configured to assist a surgeon in properly removing the head of a patient's femur during a hip replacement surgery. Embodiments of the disclosed orthopedic surgical assembly are configured to be received on a neck of a femur between a head and a shaft of the femur. The embodiments may include a base portion with a body portion defining a contoured recess, wherein the contoured recess is configured to be received adjacent a portion of the neck of the femur. A first guide plate may include a mounting tab and a cutting slot, the mounting tab being configured to be selectively coupled to the base portion so that the cutting slot is disposed adjacent the neck of the femur in a first position.

In some embodiments, the present invention discloses a kit for providing an orthopedic surgical assembly configured to be received on a neck of a femur between a head and a shaft of the femur. Such embodiments may include a patient specific base portion configured for a customized fit on the neck of the patient's femur and multiple guide plates (e.g., two or more guide plates) for use therewith that allow a physician to alter both the position and the angle of the cutting slot with regard to the neck of the patient's femur.

The present disclosure also includes methods of using the disclosed embodiments of orthopedic surgical assemblies. Such methods may include the steps of creating a 3A model of the patient's femur from a medical image, forming a base portion of the surgical assembly, selecting a desired guide plate, and coupling the guide plate to the base portion. The contoured recess of the base portion is positioned adjacent to the neck of the femur, and the neck of the femur is cut as guided by the cutting slot.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

Figure 1:
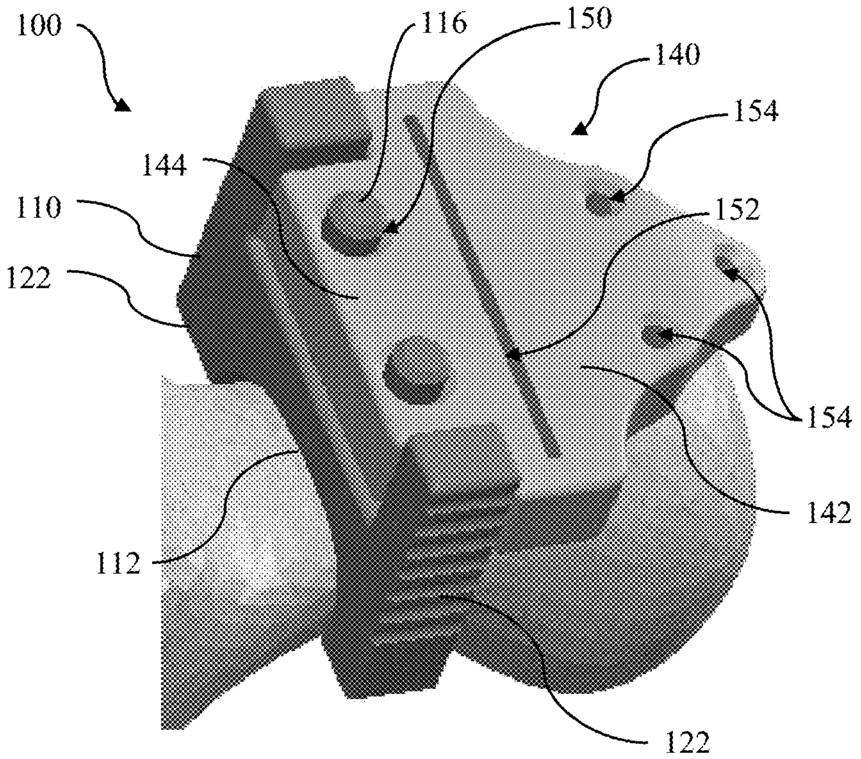
FIG. 1 is an isometric view of an embodiment of an orthopedic surgical assembly in accordance with an embodiment of the present invention.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedents "about," "substantially," or "generally," it is contemplated that values within up to 15%, up to 10%, up to 5%, or up to 1% (above or below) of the particularly stated value can be included within the scope of those aspects. In other aspects, when angular values are approximated by use of the antecedents "about," "substantially," or "generally," it is contemplated that angular values within up to 15 degrees, up to 10 degrees, up to 5 degrees, or up to one degree (above or below) of the particularly stated angular value can be included within the scope of those aspects.

In the following description and claims, wherever the word "comprise" or "include" is used, it is understood that the words "comprise" and "include" can optionally be replaced with the words "consists essentially of" or "consists of" to form another embodiment.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Figure 2A:
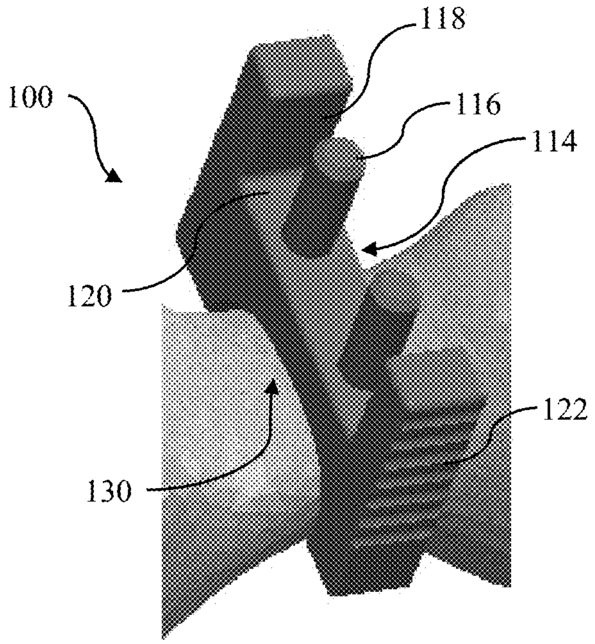
FIGS. 2A and 2B are top and bottom isometric views of the base portion of the orthopedic surgical assembly shown in FIG. 1.
Figure 2B:
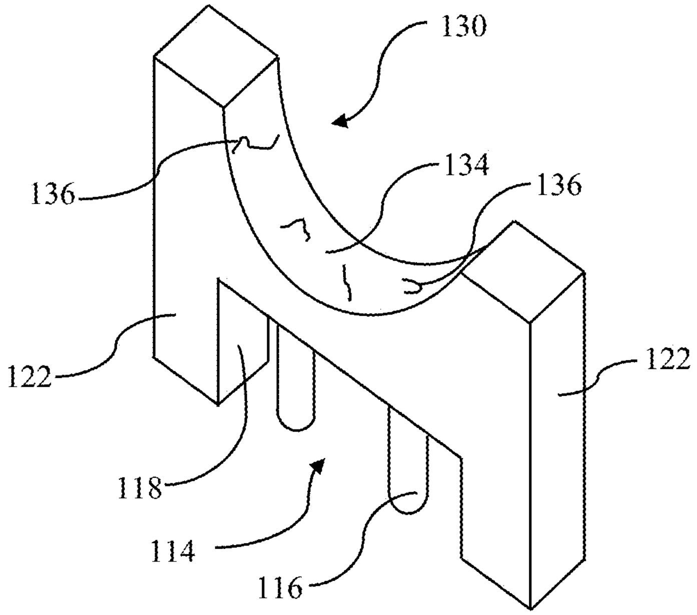
Figure 4A:
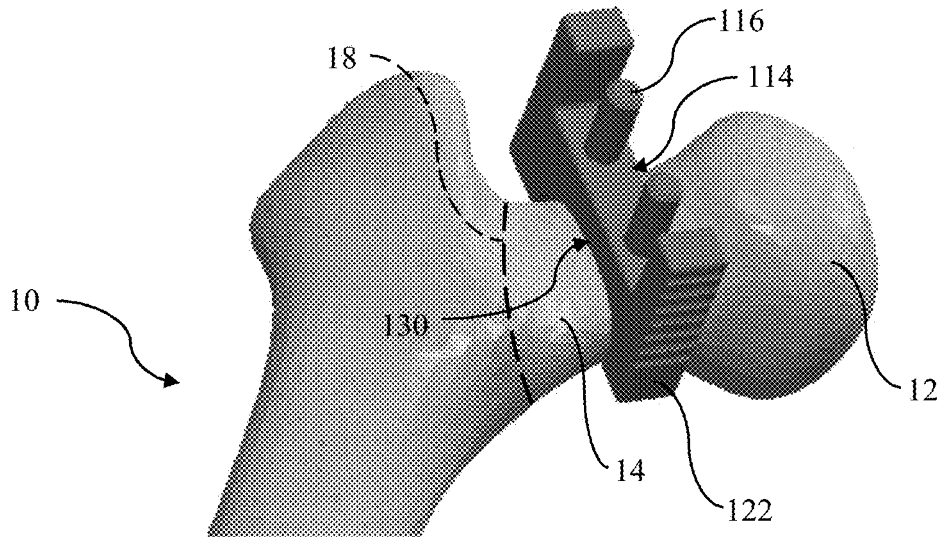
FIGS. 4A, 4B, and 4C are isometric views of the orthopedic surgical assembly shown in FIG. 1, as fitted on the neck of a femur, in accordance with an embodiment of the present invention.
Figure 6:
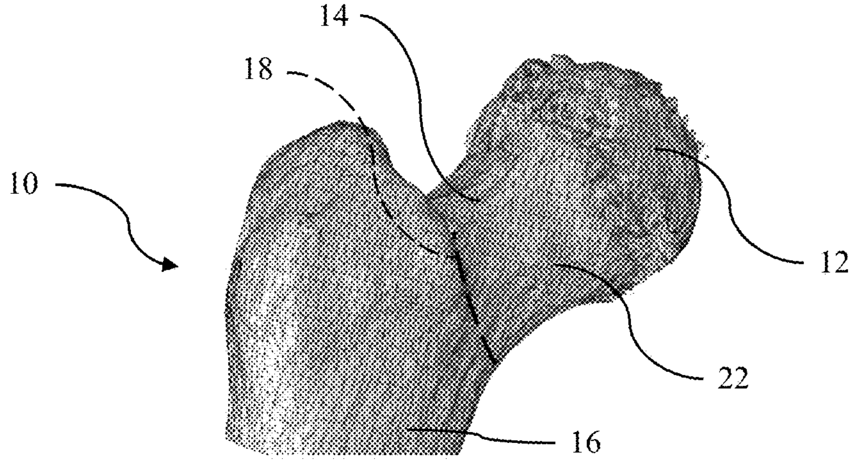
FIG. 6 is a representation of a generic femur.
Figure 7A:
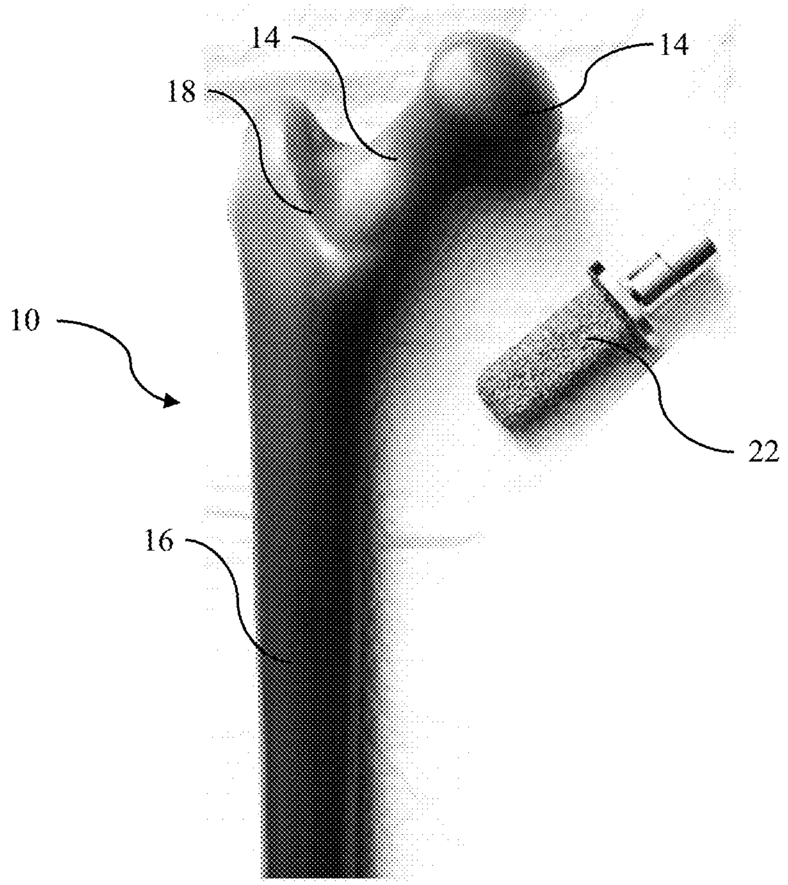
FIGS. 7A and 7B are front plain views of a portion of a femur and a surgical implant for a hip replacement surgery, both prior to removal of the head of the femur and after removal of the head and insertion of the surgical implant in the neck of the femur, respectively.
Figure 7B:
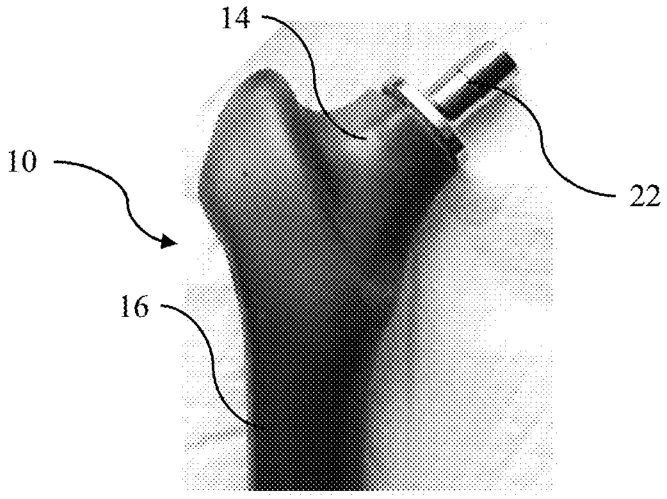

Referring now to FIG. 1, a customized patient-specific orthopedic surgical instrument may be embodied as an orthopedic surgical assembly 100, which is configured to be coupled to a femur 10 (FIG. 6) of a patient. The surgical assembly 100 includes a base portion 110 configured to be coupled to either the anterior or the posterior side of the femur 10. Referring additionally to FIGS. 2A and 2B, the base portion 110 of the surgical assembly 100 includes a body portion 110, a pair of mounting legs 122 extending therefrom, and a plate recess 114 defined opposite the mounting legs 122. As shown, the two mounting legs 122 extend orthogonally from the body portion 112 of the base portion 110 and are configured to be positioned on opposite sides of the neck 14 of the femur 10, as shown in FIG. 4A. As best seen in FIG. 2B, the base portion 110 of the surgical assembly 100 defines a contoured recess 130 that extends between the mounting legs 122 and can be substantially semi-cylindrical so as to receive a portion of the patient's femur therein. The contoured recess 130 includes a bone-contacting, or bone-facing, abutment surface 134 defined on the inside of the contoured recess 130. The bone-contacting abutment surface 134 includes one or more contours 136 that are configured to match up with contours in the surface of the patient's femur to which the surgical assembly is secured (for example, such that the one or more contours 136 are configured to receive a portion of the patient's bone having a corresponding contour). Specifically, each contour 136 can have a unique set of ridges and depressions that are shaped to engage a corresponding unique set of depressions and ridges of the outer surface of the neck 14 of the patient's femur 10. As described above, the contours of the bone-contacting abutment surface 134 allow the positioning of the base portion 110 of the surgical assembly 100 on the patient's femur 10 in a unique pre-determined location and orientation, as shown in FIG. 4A.

Figure 4B:
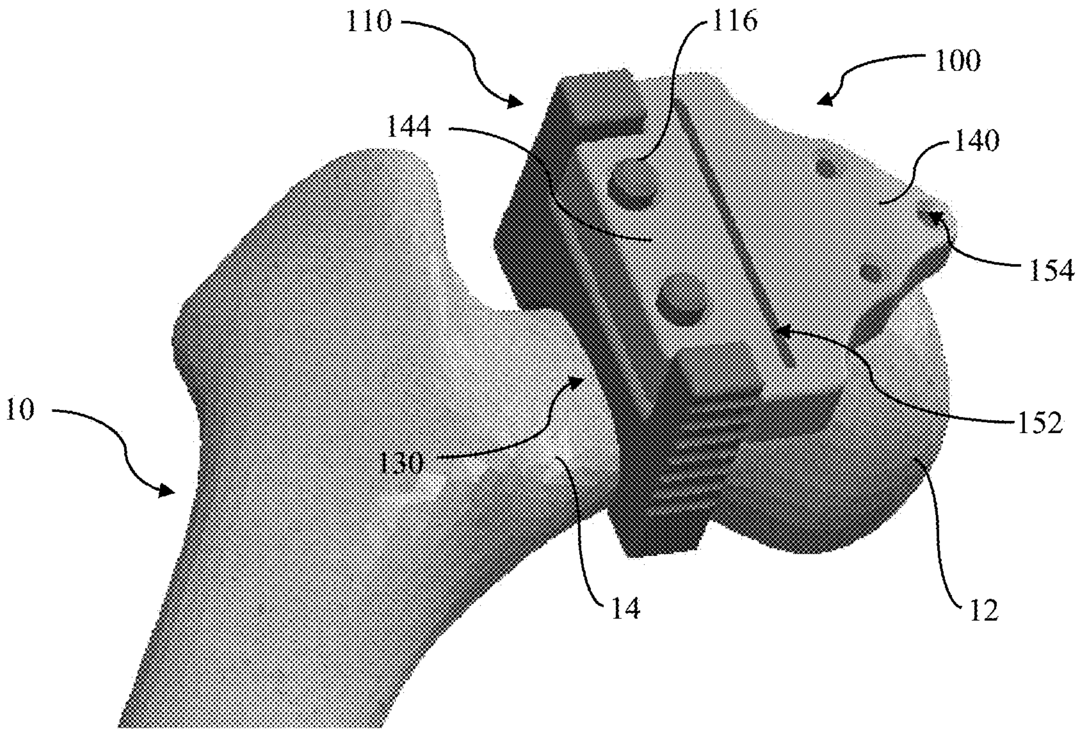
Figure 4C:
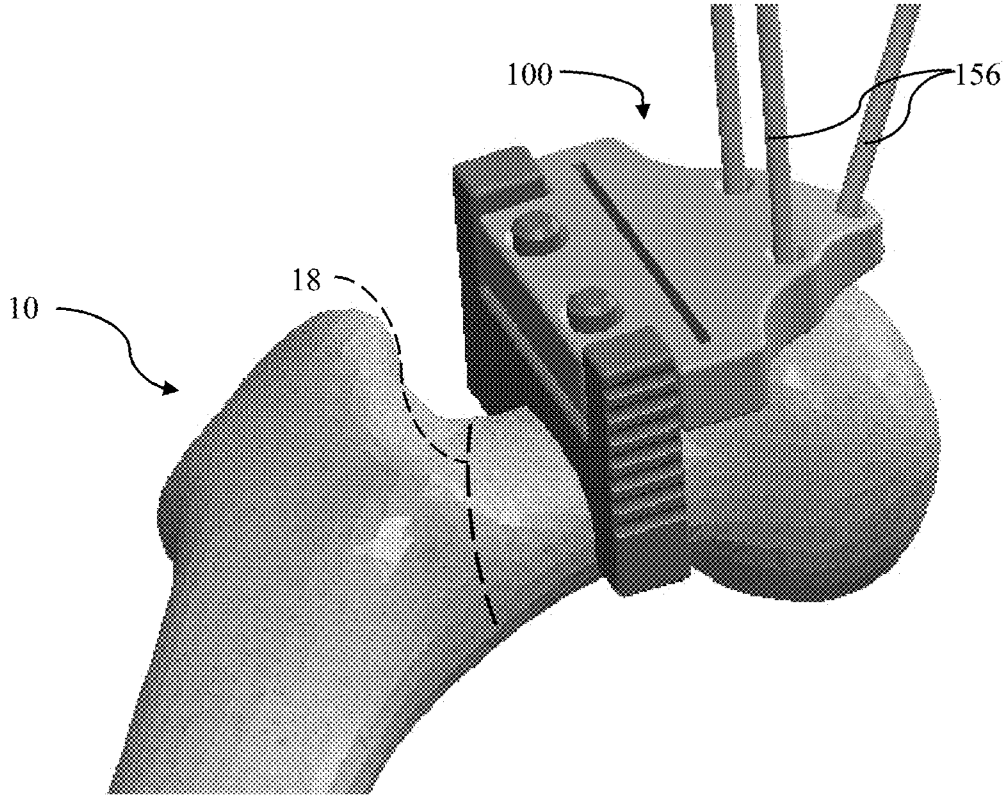

As best seen in FIGS. 2A and 4, the base portion 100 can include a mounting recess 114 that is configured to receive a portion of a corresponding guide plate 140 therein. Preferably, the mounting recess 114 is opposite the contoured recess 130 of the base portion 110 and is formed by a pair of substantially parallel side walls 118 that extend upwardly from opposite side edges of a substantially rectangular, elongate base wall 120. As shown, the side walls 118 are planar and orthogonal to the base walls 126. One or more cylindrical mounting projections 116 extend upwardly from the base wall 120 and are configured to both align and secure the corresponding guide plate 140 to the base portion 110, as shown in FIG. 4B. In the illustrative embodiment, the base portion 110 is preferably formed from a polymeric material. The polymeric material may be plastic such as, for example, polyethylene or another biocompatible plastic.

Figure 3A:
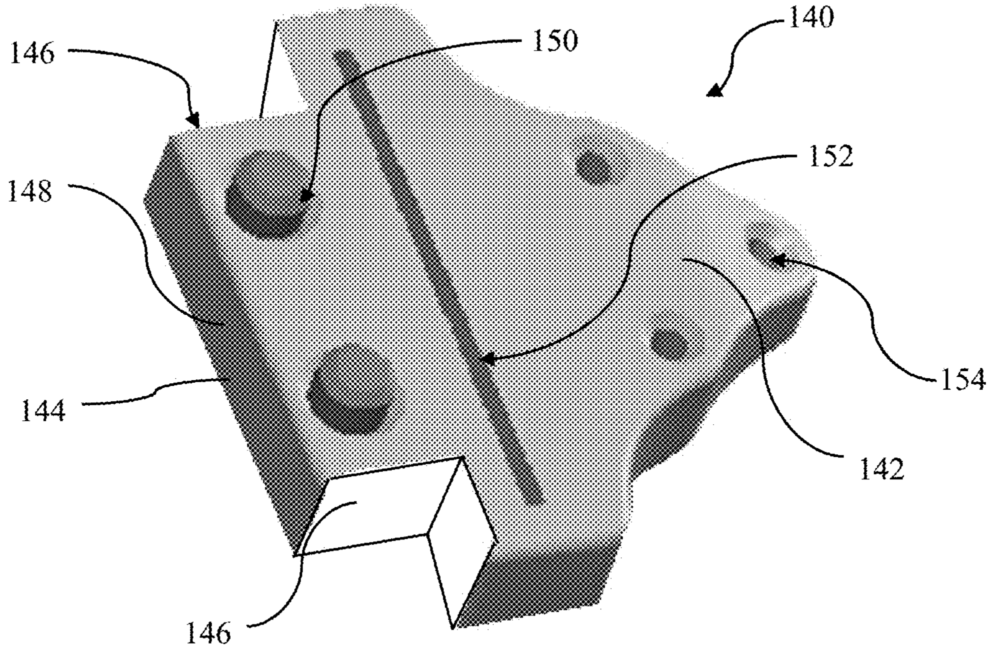
FIGS. 3A and 3B are a top isometric and side plain view, respectively, of the guide plate of an orthopedic surgical assembly shown in FIG. 1.
Figure 3B:
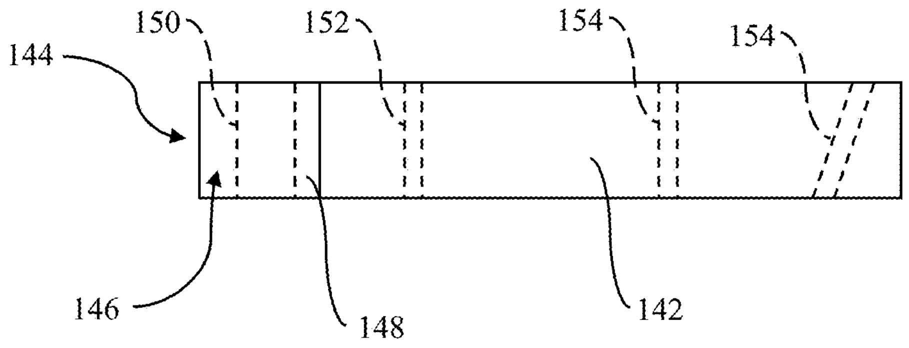

As previously noted, the orthopedic surgical assembly 100 also includes a guide plate 140, as best seen in FIGS. 3A and 3B. The guide plate 140 includes a body portion 142 defining a cutting slot 152 that extends therethrough. The cutting slot 152 can be sized to both extend across the entire width of the bone to which the surgical assembly 100 is attached and to receive a cutting blade (not shown), which a surgeon may use to resect a portion of the patient's bone. The purpose of the guide plate 140 is to ensure that the cutting slot 152 is both positioned adjacent the pre-selected area of the patient's bone, and oriented at the desired cutting angle. Thus, it is contemplated that the guide plate 140 can have a patient-specific configuration. For the present orthopedic surgical assembly 100, the cutting slot 152 can be positioned adjacent the neck 14 of the patient's femur 10. The guide plate 140 can also include a mounting tab 144 that is substantially rectangular in shape and correspondingly shaped to the mounting recess 114 of the base portion 110. Specifically, the mounting tab 144 is preferably formed by a pair of parallel side walls 146 that are orthogonal to the base wall 148 and extend upwardly from opposite edges thereof, as best seen in FIGS. 3A and 3B. As shown, a pair of mounting apertures 150 can be defined in the mounting tab 144 of the base plate 140, with each mounting aperture 150 being configured to slidably receive a corresponding mounting projection 116 therein. The receipt of the mounting projections 116 in mounting apertures 150 can ensure the mounting tab 144 of the guide plate 140 is properly seated in the mounting recess 114 of the base portion 110, meaning the guide plate 140 and base portion 110 are properly aligned. In some aspects, at least a portion of the guide plate 140 can comprise a material that differs from the material(s) of the base portion 110. For example, in some aspects, the guide plate 140 can comprise a material that is resistant to a saw received within the slot 152. Optionally, in these aspects, the slot 152 can be coated with a more durable material than the material(s) of the base portion 110, such as, for example, hardened stainless steel In some aspects, multiple fixing apertures 154 are positioned between the cutting slot 152 and the distal end of the guide plate 140 in the illustrative embodiment. Each fixing aperture 154 can be sized to receive a surgical drill (not shown), which the surgeon may use to establish pinholes in the head 12 in the femur 10. Subsequently, the fixing pins 156 can be inserted in both the fixing apertures 154 and the corresponding pinholes in the femur to fix the orthopedic surgical assembly 100 in the desired position during the cutting operation. Preferably, each guide plate 140 is constructed of stainless steel, or like biocompatible metal. As such, the slots of the guide plates are resistant to damage by the surgeon's cutting blade and the guide plates may be sterilized for repeated use with different patients.

Figure 5:
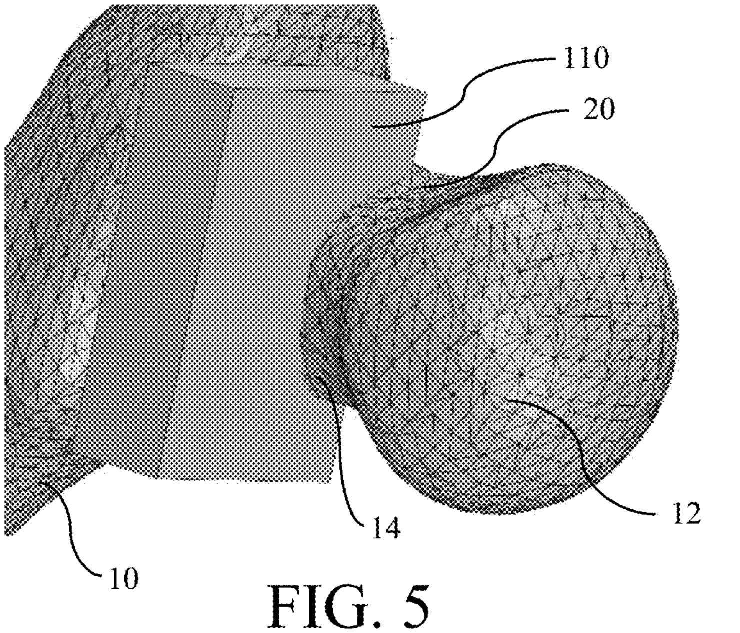
FIG. 5 is an isometric view of the base portion of the orthopedic surgical assembly shown in FIG. 1, during creation of the contoured recess.

In use, the disclosed embodiments of orthopedic surgical assemblies 100 may be used to position the cutting slot 152 adjacent the neck 14 of a patient's femur 10 between the intertrochanteric line 18 and head 12 of the femur 10. Prior to constructing the base portion 110 of the surgical assembly 100, a scan (e.g., an imaging scan) of the concerned area of the patient's femur is made, and 3D imaging software may be used to produce the contoured recess 130 of the base portion 110 (FIG. 5). Using the imaging software, the base position 110 may be created by a method such as, but not limited to, 3D printing. Although the surface 134 of each base portion's contoured recess 130 is patient specific, the configuration of the mounting recesses 114 are the same from base portion to base portion. As such, should a surgeon decide the originally selected position of the cutting slot 152 with regard to the neck 14 of the femur 10 is not ideal, the surgeon may interchange the original guide plate 140 for an alternate one (a second guide plate) having a different guide slot 152 position. As such, the position of the cutting slot 152 may be altered without having to re-produce the base portion 110, thereby saving both time and expense.

Accordingly, in exemplary aspects, a kit for providing an orthopedic surgical assembly can be provided. The kit can include a base portion having a body portion defining a contoured recess, wherein the contoured recess is configured to be received adjacent a portion of the neck of the femur. The kit can further comprise a plurality of guide plates, which can include at least a first guide plate and a second guide plate. Each of the guide plates can define a respective cutting slot and be configured to be selectively secured to the base portion so that the cutting slot of the guide plate is disposed adjacent the neck of the femur in a respective position. Thus, for example, the cutting slot of the first guide plate can be disposed adjacent the neck of the femur in a first position, and the cutting slot of the second guide plate can be disposed adjacent the neck of the femur in a second position that is different than the first position (for example, different by spacing of the slot from the femur (or other location), dimension(s) of the slot, angular orientation of the slot, combinations thereof, and the like). In exemplary aspects, the kit can further comprise packaging for receiving the components of the kit. In still further aspects, the kit can comprise instructions for use of the kit, which can optionally be positioned within or associated with the packaging.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An orthopedic surgical assembly configured to be received on a neck of a femur between a ball and a shaft of the femur, comprising:

a base portion including a body portion defining a contoured recess, wherein the contoured recess is configured to be received adjacent a portion of the neck of the femur; and a first guide plate including a mounting tab and a cutting slot, the mounting tab being configured to be selectively coupled to the base portion so that the cutting slot is disposed adjacent the neck of the femur in a first position.

Aspect 2: The orthopedic surgical assembly of aspect 1, wherein the body portion of the base portion further defines a mounting recess, wherein the mounting tab is configured to be received within the mounting recess.

Aspect 3: The orthopedic surgical assembly of aspect 2, wherein the base portion further comprises a pair of projections extending from the body portion, each projection having a side wall, wherein a base wall extends between the side walls of the projections and defines the mounting recess.

Aspect 4: The orthopedic surgical assembly of aspect 3, wherein the mounting tab of the first guide plate includes a pair of side walls and a base wall extending therebetween, and wherein the side walls of the projections and the side walls of the mounting tab are configured to abut each other.

Aspect 5: The orthopedic surgical assembly of aspect 4, wherein the base walls of the mounting recess and the mounting tab are substantially planar, and wherein the side walls of the mounting recess and the mounting tab are substantially parallel to each other.

Aspect 6: The orthopedic surgical assembly of aspect 4, wherein the mounting recess further comprises at least one mounting projection extending upwardly from the base wall of the mounting recess, wherein the mounting tab of the first guide plate defines at least one mounting aperture, and wherein each mounting aperture of the at least one the mounting aperture is configured to receive a respective mounting projection of the at least one mounting projection therein.

Aspect 7: The orthopedic surgical assembly of aspect 6, wherein the at least one mounting aperture further comprises a pair of mounting apertures and the at least one mounting projection further comprises a pair of mounting projections.

Aspect 8: The orthopedic surgical assembly of any one of the preceding aspects, wherein the contoured recess includes a mounting surface that is conformed to a portion of an outer surface of the neck of the femur.

Aspect 9: The orthopedic surgical assembly of aspect 8, wherein the mounting surface of the contoured recess is patient-specific.

Aspect 10: The orthopedic surgical assembly of aspect 9, wherein mounting surface of the contoured recess is based on a medical image.

Aspect 11: The orthopedic surgical assembly of aspect 8, wherein the mounting surface of the contoured recess extends between a pair of legs that extend from the base portion.

Aspect 12: The orthopedic surgical assembly of any one of the preceding aspects, further comprising:

at least one fixing aperture defined in a distal end the first guide plate; and a fixing pin that is configured to pass through the at least one fixing aperture of the first and be inserted into the ball of the femur.

Aspect 13: The orthopedic surgical assembly of any one of the preceding aspects, wherein the cutting slot of the first guide plate is configured to extend across an entire width of the neck of the femur at the first position.

Aspect 14: The orthopedic surgical assembly of any one of the preceding aspects, wherein the base portion comprises a first material, wherein the first guide plate comprises a second material that is different from the first material.

Aspect 15: The orthopedic surgical assembly of aspect 14, where in the first material is a biocompatible polymer and the second material is a biocompatible metal.

Aspect 16: The orthopedic surgical assembly of any one of the preceding aspects, wherein the base portion is 3D printed.

Aspect 17: The orthopedic surgical assembly of any one of the preceding aspects, wherein the first guide plate is configured to be sterilized and reused.

Aspect 18: The orthopedic surgical assembly of any one of the preceding aspects, wherein the contoured recess is configured to be received on the neck of the femur at a location that is spaced between the neck and an intertrochanteric line of the femur.

Aspect 19: The orthopedic surgical assembly of any one of the preceding aspects, wherein the first location is at a narrowest portion of the neck of the femur.

Aspect 20: The orthopedic surgical assembly of any one of the preceding aspects, wherein the cutting slot of the first guide plate is configured to permit receipt of a saw at a predetermined angle.

Aspect 21: The orthopedic surgical assembly of aspect 20, wherein the predetermined angle is 90° to the longitudinal axis of the neck of the femur.

Aspect 22: The orthopedic surgical assembly of any one of the preceding aspects, wherein the first guide plate is patient-specific.

Aspect 23: The orthopedic surgical assembly of aspect 22, wherein the first guide plate has a contoured surface that is configured to engage a portion of the femur.

Aspect 24: The orthopedic surgical assembly of any one of the preceding aspects, wherein an entirety of the contoured recess is configured to be positioned between a junction of the femoral head and the neck and an intertrochanteric line of the femur.

Aspect 25: A kit for providing an orthopedic surgical assembly configured to be received on a neck of a femur between a ball and a shaft of the femur, comprising:

a base portion including a body portion defining a contoured recess, wherein the contoured recess is configured to be received adjacent a portion of the neck of the femur;

a first guide plate defining a cutting slot, the first guide plate being configured to be selectively secured to the base portion so that the cutting slot is disposed adjacent the neck of the femur in a first position; and a second guide plate defining a cutting slot, the second guide plate being configured to be selectively secured to the base portion so that the cutting slot is disposed adjacent the neck of the femur in a second position, wherein the second position differs from the first position.

Aspect 26: The kit of aspect 24, wherein the base portion further comprises a pair of projections extending from the body portion, each projection having a side wall, wherein a base wall extends between the side walls of the projections and defines the mounting recess, and wherein the first guide plate and the second guide plate each include a mounting tab that is selectively receivable within the mounting recess.

Aspect 27: The kit of aspect 25, wherein the mounting tabs of the first guide plate and the second guide plate include a pair of side walls and a base wall extending therebetween, and the side walls of the projections and the side walls of the mounting tabs are configured to abut each other.

Aspect 28: The kit of aspect 26, wherein the base walls of the mounting recess and the mounting tabs are substantially planar, and the side walls of the mounting recess and the mounting tab are substantially parallel to each other.

Aspect 29: The kit of aspect 26, wherein the mounting recess further comprises at least one mounting projection extending upwardly from the base wall of the mounting recess, and the mounting tabs of the first guide plate and the second guide plate each define at least one mounting aperture, wherein the mounting apertures as are configured to receive the projection therein.

Aspect 30: The kit of aspect 28, wherein the at least one mounting aperture of the first guide plate and the second guide plate comprise a pair of mounting apertures and the at least one mounting projection comprises a pair of mounting projections.

Aspect 31: The kit of aspect 24, wherein the contoured recess includes a mounting surface that is conformed to a portion of an outer surface of the neck of the femur.

Aspect 32: The kit of aspect 24, further comprising:

at least one fixing aperture defined in a distal end of both the first and the second guide plates; and a fixing pin that is configured to pass through the at least one fixing aperture of the first and the second guide plate and be inserted into the ball of the femur.

Aspect 33: The kit of aspect 24, wherein the mounting tabs of the first guide plate and the second guide plate have the same dimensions.

Aspect 34: A method of using the orthopedic surgical assembly of any one of aspects 1-23, the method comprising:

coupling the base portion to the first guide plate;

positioning the contoured recess against a neck of a femur between a ball and a shaft of the femur; and cutting the neck of the femur through the cutting slot.

Aspect 35: A method of making the orthopedic surgical assembly of any one of aspects 1-23, the method comprising:

creating a 3D model of the base portion based in part on a medical image of the femur; and forming the base portion from the 3D model.

Although the foregoing invention has been described in some detail by way of illustration and example for purposes of clarity of understanding, certain changes and modifications may be practiced within the scope of the appended claims.

What is claimed is:

1. A method of using an orthopedic surgical assembly, the method comprising:

coupling a base portion to a first guide plate, wherein the base portion includes a body portion defining a contoured recess, wherein the contoured recess is configured to be received adjacent a portion of a neck of a femur, wherein the first guide plate includes a mounting tab and a cutting slot, the mounting tab being configured to be selectively coupled to the base portion so that the cutting slot is disposed adjacent the neck of the femur in a first position;

positioning the contoured recess against a neck of a femur between a ball and a shaft of the femur so that the cutting slot is positioned between the ball of the femur and an entirety of the contoured recess along an axis extending between the mounting tab and the cutting slot of the first guide plate; and cutting the neck of the femur through the cutting slot.

2. The method of claim 1, wherein positioning the contoured recess against a neck of a femur between a ball and a shaft of the femur comprises positioning the contoured recess at a location that is spaced between the neck and an intertrochanteric line of the femur.

3. The method of claim 1, wherein positioning the contoured recess against a neck of a femur between a ball and a shaft of the femur comprises positioning the contoured recess between a junction of the femoral head and the neck and an intertrochanteric line of the femur.

4. The method of claim 1, wherein the cutting slot of the first guide plate extends across an entire width of the neck of the femur at the first position.

5. The method of claim 1, wherein the first guide plate is configured for sterilization and reuse with different patients.

6. The method of claim 1, wherein coupling the base portion to the first guide plate further comprises positioning the mounting tab within a mounting recess defined by the base portion.

7. The method of claim 6, wherein the base portion further comprises a pair of projections extending from the body portion, each projection having a side wall, wherein a base wall extends between the side walls of the projections and defines the mounting recess.

8. The method of claim 1, wherein the contoured recess includes a mounting surface that is conformed to a portion of an outer surface of the neck of the femur.

9. The method of claim 8, wherein the mounting surface of the contoured recess is patient-specific, wherein the mounting surface of the contoured recess is based on a medical image.

10. The method of claim 8, wherein the mounting surface of the contoured recess extends between a pair of legs that extend from the base portion.

11. The method of claim 1, wherein positioning the contoured recess against a neck of a femur further comprises:

passing a fixing pin through at least one fixing aperture defined in a distal end of the first guide plate; and inserting the fixing pin into the ball of the femur.

12. The method of claim 1, wherein the base portion comprises a first material, and wherein the first guide plate comprises a second material that is different from the first material.

13. The method of claim 12, wherein the first material is a biocompatible polymer and the second material is a biocompatible metal.

14. The method of claim 1, wherein the base portion is 3D printed.

15. The method of claim 1, wherein the cutting slot of the first guide plate is configured to permit receipt of a saw at a predetermined angle.

16. The method of claim 15, wherein the predetermined angle is 90° to a longitudinal axis of the neck of the femur.

* * * * *